United States Patent [19]

Taylor

[11] 4,126,701

[45] Nov. 21, 1978

[54] PROCESS OF SPARING POULTRY FROM THE EFFECT OF TOXINS

[75] Inventor: Gregg W. Taylor, Murrayville, Ga.

[73] Assignee: A.H.P., Inc., Gainesville, Ga.

[21] Appl. No.: 814,100

[22] Filed: Jul. 8, 1977

Related U.S. Application Data

[63] Continuation-in-part of Ser. No. 625,693, Oct. 24, 1975, abandoned, which is a continuation-in-part of Ser. No. 595,876, Jul. 14, 1975, abandoned, which is a continuation-in-part of Ser. No. 454,000, Mar. 22, 1974, Pat. No. 3,915,637, which is a continuation-in-part of Ser. No. 342,290, Mar. 16, 1973, Pat. No. 3,916,027.

[51] Int. Cl.$^2$ ............................................. A61K 31/14
[52] U.S. Cl. ..................................................... 424/329
[58] Field of Search ......................................... 424/329

[56] References Cited

U.S. PATENT DOCUMENTS 3,231,466   1/1966   Hoffman et al. ...................... 424/329

*Primary Examiner*—Sam Rosen
*Attorney, Agent, or Firm*—Watson, Cole, Grindle & Watson

[57] ABSTRACT

A process of feeding animals and poultry a complete feed consisting only of (i) between 0.00077 and 0.005 percent by weight, based on the weight of the feed, of gentian violet and (ii) the remainder medically inert ingredients, such inert ingredients not having a sparing effect for poultry and animals from the toxic and/or lethal effects of aflatoxin. The gentian violet has the effect of sparing animals and poultry from the toxic effects of aflatoxins in feeds. The inert ingredients include all of the inert ingredients normally in a complete or basal animal or poultry feed.

7 Claims, No Drawings

PROCESS OF SPARING POULTRY FROM THE EFFECT OF TOXINS

This application is a continuation-in-part application of applicant's copending application Ser. No. 625,693, now abandoned, filed on Oct. 24, 1975, which in turn was a continuation-in-part of applicant's then co-pending application Ser. No. 595,876, now abandoned, filed July 14, 1975, which in turn is a continuation-in-part of two others of applicant's applications which were co-pending therewith, Ser. No. 454,000, filed Mar. 22, 1974, now U.S. Pat. No. 3,915,637, and application Ser. No. 342,290, filed Mar. 16, 1973, now U.S. Pat. No. 3,916,027

BACKGROUND OF THIS INVENTION

1. Field of This Invention

This invention relates to animal and poultry feed which contains a medicinal agent that is a selective fungicidal mold inhibitor of Candida albicans. This invention also relates to the use of such feed to spare animals and poultry from the toxic effects of aflatoxins and other mycotoxins in feed.

2. Art Section

It is known that a given strain of mold may gain or lose its ability to produce toxins without known reason. Several reasons for this phenomenon have been advanced, namely, change of substrate, genetics, stage of growth, accumulation and metabolism of the toxin, and actual stability of the toxin.

Facial eczema of sheep in New Zealand has been caused by *Pithomyces chartarus* — the toxin caused liver damage and skin disorders. A malady in horses, cattle, and poultry has been caused by a toxin from a mold called *Stachybotrys atra*. A field outbreak in Georgia of mold toxicosis in swine resulted from corn left in the field — the toxic molds were *Aspergillus flavus* and *Penicillium rubrum*. A massive outbreak of toxicity from moldy ground nut meal (peanut) occurred in England — the toxin producing mold was a strain of *Aspergillus flavus*. The common name applied to the disease is "Turkey X" disease, and the poisonous material has been designated as "Aflatoxin." Aflatoxin has carcinogenic properties. Hemorrhagic disease in chicks occurred — toxins from certain molds will cause lesions indistinguishable from field hemorrhagic disease. Bovine hyperkeratosis has been caused by *Aspergillus clavatus*. A toxicosis from moldy feed at Texas Agricultural Experimental Station was caused by unidentified molds. The mold brought on acute lysine deficiency. Arginine was similarly affected. These amino acids alleviated most of the problem in poults.

Forgacs wrote in 1954 that aflatoxin was a feed mold problem.

Aflatoxicosis is recognized as a toxic disease problem occurring as a result of fungus growth in feeds and feedstuffs. Even if the fungus is killed in the feedstuffs the aflatoxin that has been produced by the growing fungus remains in the feed as a poison which then produces the symptoms of aflatoxicosis when the basal feed is ingested by poultry. There is a need for an effective active ingredient to be added to the inert ingredients of the basal feed to effect a reduction or "sparing effect" in the consuming poultry from the poisonous affects of the aflatoxin-containing feed. Such a sparing effect is obviously not produced by the ingredients which normally comprise a basal poultry feed, hence such ingredients are "inert" re the aflatoxicosis problem.

Aflatoxin, produced by *Aspergillus flavus*, causes Turkey X disease. The duck is most susceptible, followed by the turkey and chicken in that order.

Fungal growth can occur in ground grains having as little as 12 percent moisture. The heat and moisture given off by fungal growth activity encourages more fungal growth. Mold growth often occurs which causes certain molds to produce mycotoxins. Several of these mycotoxins are quite toxic and present a serious problem to animals and poultry by death, loss of weight or lessened weight gain, etc. Chronic mycotoxicoses from the long term low intake of mycotoxins often cause reduced growth rate and appetite, among other things. Recovery is slow even when switched to feeds free of mycotoxins. Another danger is that aflatoxin has been demonstrated to be a carcinogen. Mycotoxins, and aflatoxin in particular, are difficult to remove from feedstuffs. Heat is ineffective; U.V. irradiation and solvent extraction are effective, but quite economically unfeasible. Certain acids, bases and other compounds have been used to neutralize aflatoxin in feed, but most of such compounds appear to have been unsatisfactory for a number of reasons.

BROAD DESCRIPTION OF THIS INVENTION

An object of this invention is to provide a process for sparing animals and/or poultry from the toxic and/or lethal effects of mycotoxins, such as aflatoxins, in feed. Another object of this invention is to provide a composition for animals and/or poultry which has the property of sparing animals and/or poultry from the toxic and/or lethal effects of mycotoxins, such as aflatoxins, in feeds. Other objects and advantages are set out herein or are obvious herefrom to one ordinarily skilled in the art.

Such objects and inventions are achieved by the process and composition of this invention.

This invention involves a method for sparing an animal or poultry from the toxic and/or effects of a mycotoxin, such as an aflatoxin, in an animal or poultry feed. The method includes feeding a complete feed to the animal or poultry, the complete feed being comprised of (i) gentian violet and (ii) the remainder medically inert ingredients. The gentian violet spares the animal or poultry from the toxic and/or lethal effects of mycotoxin in the feed as a contaminant. the gentian violet is present in the feed in an amount between 0.00077 and 0.005 percent by weight, based on the weight of the complete feed. The medically inert ingredients do not have a sparing effect for poultry and animals from the toxic and/or lethal effects of mycotoxins.

The composition of this invention is preferably formulated by adding a premix concentrate to the feed. The premix contains between 0.1 and 10 percent by weight of gentian violet and the remainder medically inert ingredients. Enough of the premix concentrate to the other ingredients of the feed is used to obtain the recited amount of gentian violet in the complete feed. Other methods of preparing the complete feed can be used, for example, the gentian violet, by itself, can be directly admixed to the feed.

Preferably the feed contains between 0.00155 and 0.00232 percent by weight of gentian violet, based on the weight of the complete poultry feed.

This invention is quite useful for feeds that are contaminated with as much as 10 p.p.m. or more of mycotoxin, such as aflatoxin.

The sparing effect of gentian violet appears to be a linear function of the concentration of the aflatoxin in the feed.

The weight depression of animals or poultry eating mycotoxin-contaminated animal or poultry feeds which contain gentian violet at the disclosed levels is significantly less than for animals or poultry eating such mycotoxin-contaminated feed which does not contain gentian violet.

The levels of gentian violet used in this invention are low enough not to damage the consuming animal or poultry and not to produce an unacceptable residue in food from the animal or poultry. The level of residue is extremely low, particularly when a short withdrawal period is used before slaughter.

Gentian violet is essentially non-absorbable and stable at the pH range of the digestive tract of animals and poultry.

Other substituted benzophenone azoanilide dyes or rosaniline base dyes can be used in place of the gentian violet. Such are also known as triaminotritane dyes related to rosaniline. The $-N(CH_3)_2$ groups of gentian violet can be replaced by other auxochrome groups such as $-OH$, $-NH_2$, $-N(C_2H_5)_2$, etc. The other various substituents, and the substituents on gentian violet, can be located at any position on the three benzyl rings. The other dyes must have at least one amino chloride group and/or substituted amino chloride group.

Examples of such other substituted benzophenone azoanilide dyes are: pentamethylpararosaniline chloride; tetramethylpararosaniline chloride; methyl green or light green, which is the methyl chloride addition product of gentian violet; ethyl green, which is the ethyl chloride addition product of gentian violet; sulfonic acids of the rosanilines, such as water blue and patent blue; phenylated rosanilines, such as triphenyl fuchsin, aniline blue, diphenylamine blue and spirit blue; pararosaniline; mixtures of pararosaniline with its methyl homologs, such as fuchsins and magentas. More broadly, any triphenylmethane dye that contains an amino group or substituted amino group can be used in place of gentian violet. Examples of such triphenylmethane dyes are the malachite green series of dyes, such as malachite green.

Most of such aniline dyes are rather toxic, but can be readily used if they are buffered by any generally non-toxic conventional buffering system to reduce their toxicity. The buffering system can be one composed from alkali and acid salts of phosphoric acid, acetic acid, carbonic acid and/or citric acid. Usually the buffer salts are the monobasic and tribasic salts thereof.

For the best effects the feed composition of this invention is fed to poultry, hogs or cattle.

Any complete poultry feed or basal poultry feed can be used. It can contain, for example, ground yellow corn, soybean oil meal, steamed bone meal, ground limestone, iodized salt, manganese sulfate, Vitamin A oil, dry Vitamin D-3, riboflavin, Vitamin B-12 and niacin. It can also contain, for example, fish meal and meat meal.

Any complete animal feed or basal animal feed can be used; it can contain, for example, any of the following ingredients: iodized salt, dry Vitamin D-3, riboflavin, Vitamin B-12, niacin, meat meal, D calcium pantothenate, cracked or milled grains such as corn, wheat, oats, barley and the like, dried molasses, dried sorghum, soybean meal, cottonseed meal, peanut meal, fish meal, essential amino acids, such as lysine, peptides and polypeptides containing essential amino acids, casein, soya bean protein, vitamins such as Vitamins A, D, E and K, mineral nutrients such as sodium chloride, ferrous salts, magnesium sulfate and calcium salts, proteins, buffers, dextrose, sucrose, lactose, maltose, corn syrup solids, hydrolized cereal solids, hay, etc.

The following is a typical or standard vitamin premix that is used in a complete poultry feed:

|  | gm/100 lb. |
|---|---|
| Manganese sulfate (feed grade) | 11.4 |
| Vitamin A oil (10,000 I.U./gm) | 22.7 |
| Dry Vitamin D-3 (1,6550 I.C.U./gm) | 22.7 |
| Riboflavin | 0.15 |
| Vitamin B-12 (3 mg. lb.) | 45.4 |
| Niacin | 1.0 |

An exemplary cattle feed is 73 percent rolled shelled corn, 20 percent ground corn cobs, and a supplement containing soybean meal, alfalfa meal, cane molasses, urea, salt, dicalcium phosphate, Vitamin A concentrate and Vitamin D concentrate.

The greatest mycotoxin effect sparing is achieved in young, maturing animals or poultry, although excellent mycotoxin effect sparing is achieved in grown mature animals or poultry.

An important feature of this invention is that there is little or no residue of the gentian violet in the tissue of the animals fed the compositions of this invention—this is apparently so due, in part, to the levels of gentian violet used in the compositions of this invention. This means that there is no toxicological danger to animals or humans from ingestion of the edible tissues of animals which have been fed the compositions of this invention.

Applicant's disclosed concentration ranges in the animal and poultry feeds are important re efficacy, i.e., mycotoxin effect sparing in poultry or animals. If amounts lower than applicant's disclosed ranges are used, there is little or no efficacy in aflatoxin effect sparing. If an amount of gentian violet is used which is higher than applicant's disclosed range (in feed), then toxic effects in the poultry can be encountered. Obviously, the lower the amount of gentian violet used, the less chance of toxic effect. The toxic effect can kill the poultry or cause a decrease in the weight gain of the poultry, which represents a serious economic loss to commercial poultry raisers. The residue build up is a potential health hazard when such higher levels are used.

DETAILED DESCRIPTION OF THE INVENTION

As used herein, the term "poultry" means domestic fowls including chickens, ducks, turkeys, geese, etc.

As used herein, the term "animal" includes domestic pigs, other swine, cattle, sheep, goats, fish, such as trout, rabbits, etc.

As used herein, the term "gentian violet" is hexamethylpararosaniline chloride or a mixture of at least 96 percent of hexamethylpararosaniline chloride with minor portions of pentamethylpararosaniline chloride and/or tetramethylpararosaniline chloride, and preferably meeting all specifications of quality for U.S.P. grade as listed in the United States Pharmacopiea XIV. This assures that none of the deadly heavy metals are left as a residue in animal or poultry tissue that is to be consumed by man.

Gentian violet is a dark green powder or greenish, glistening pieces with a metallic luster. Gentian violet is soluble in water, chloroform and ethanol. Other names for gentian violet are methylrosaniline chloride and crystal violet.

Gentian violet, both as a contaminant in water and as a residue in poultry manure, is biodegradable in the presence of the ultra-violet rays of sunlight.

Toxicosis is a pathological condition caused by the action of a toxin. Toxin is a colloidal proteinaceous poisonous substance that is a specific product of the metabolic activities of a living organism.

A large number of toxins, broadly classed as mycotoxins, are produced by a variety of molds, fungi and yeast. These toxins have been proven to interfere with normal function of poultry and animals even to producing death. Prior to this invention, all efforts to overcome the harmful effects of these mycotoxins have proven fruitless.

The discovery of this invention is that when gentian violet is administered in the feed or drinking water at the proper dosage level, the gentian violet will exert a sparing effect from the mycotoxins to alleviate their harmful effect to poultry or other animals. Some of the mycotoxin producers are: *Aspergillus* sp., *Fusarium* sp., *Alternaria* sp., *Penicillium* sp., *Mucor* sp., *Cladosporium* sp. and *Gibberella* sp.

Examples of specific molds which cause mycotoxicoses in animals and poultry are: *Aspergillus chevalieri, A. clavatus, A. flavus, A. fumigatus, A. glaucus, Paecilomyces varioti, Penicillium citrinum, P. purpurogenum, P. rubrum,* a species of *Alternaria.* Mycotoxin F-2 is produced by *Fusarium graminearium, F. moniliforme* and *F. roseum;* F-3 and F-5-3 are produced by *F. graminearum;* aflatoxin is produced by *Aspergillus flavus, A. parasiticus, A. ruber, A. wenti, A. oryzae, A. niger, A. ostianus, A. ochraceus, Penicillium puberulum, P. variable, P. citrinum, P. frequentanus,* and *Rhizopus sp.;* ochratoxin is produced by *A. ochraceus;* rubitoxin is produced by *P. rubrum;* ergot is produced by *Claviceps purpurea;* alimentary toxic aleukia is produced by *F. sporotrichiodes* and *F. tricinctum;* islandotoxin is produced by *Pencillium islandicum;* slaframine is produced by *Rhizoctonia leguminicola;* ipomeamarone is produced by *Ceratosystic fimbriata;* patulin is produced by *P. urticae;* maltoryzine is produced by A. oryzae; gliotoxin is produced by *P. terlikowskii* and *Tricoderma viride;* sporidesmin is produced by *Pithomyces chartarum;* chetomin is produced by *Chetomium cochliodes;* furocoumarins is produced by *Sclerotinia sclerotiorum;* kojic acid is produced by *A. tamarii* and *A. oryzae;* citreo-viridin is produced by P. citreo-viride; citrinin is produced by *P. citrinum and A. terrus;* and rugulosin is produced by *P. rugulosum.*

Mycotoxins (especially aflatoxins) are carcinogenic in or cause cancer in man, and so the presence of mycotoxins in the digestive trace (hence, possibly the flesh) of animals or poultry slaughtered for human consumption raises the specter of such a problem in the consuming person.

Aflatoxins are a type of mycotoxin and are produced primarily by certain strains of a group of fungi called *Aspergillus flavus.*

Aflatoxin is soluble in various lipid solvents.

Aflatoxin B-1 is the most toxic of the known mycotoxins, so the sparing effect of this invention has been primarily shown with such aflatoxin. It has been reported that 1 or 2 p.p.m., or less, of aflatoxin B-1 in feed is lethal to animals and poultry. (Pages 2, 3 and 6 of Wilcox, et al., ibid., sets out examples in various animals and poultry and discusses some F.D.A. levels in this field. As little as 0.4 p.p.b. in fish food has triggered the development of hepatic tumors in trout.) This invention has a significant sparing effect on poultry as high as 10 p.p.m. of aflatoxin in feed fed to poultry over many weeks.

Aflatoxin B. ($C_{17}H_{12}O_6$: mol wt 312.27; C, 65.38%; H, 3.87%; 0 30.74%) is the toxic metabolite of the fungus *Aspergillus flavus* Link ex Fries and is the causative principle of turkey "X" disease. It has the structure:

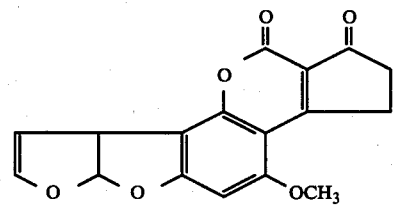

Aflatoxin B: crystals mp of 268° to 269°; exhibits blue fluoroescence; $[a]_D$ −558° (in chloroform); absorption max in ethanol: 223, 265, 362 mu (25,600, 13,400, 21,800); and $LD_{50}$ orally in white pekin ducklings: 28.2 ug.

Aflatoxin G ($C_{17}H_{12}O_7$; mol wt 328.27; C, 62.20%; H, 3.68%; 0, 34.12%) is the toxic metabolite of the fungus *Aspergillus flacus* Link ex Fries. It has the structure:

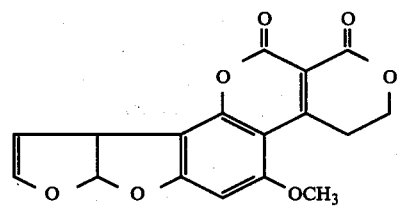

Aflatoxin G: crystals, mp of 244° to 246°; exhibits yellow-green fluorescence; $[a]_D$ −556° (in chloroform) absorption max in ethanol: 243, 257, 264, 362 mu (11,500, 9,900, 10,000, 16,100); $LD_{50}$ orally in white pekin ducklings 90 ug.

Staphylococcal infections are common in poultry. Staphylococccus bacteria are quite common in animal populations, however certain factors promote the invasion of the bacteria resulting in infections. Some mycotoxins have been shown to induce lesions of the skin and mucous membranes or cause damages to the intestinal lining. In either case, entry of staphylococcus may be promoted. See *Poultry,* Feedstuffs, June 9, 1985, p. 18. The use of gentian violet (in the amount of this invention) in poultry feed contaminated with mycotoxins eliminates or greatly lessens the effects of the mycotoxins, hence the staphylococcal infections due to mycotoxin contaminated poultry feeds are eliminated or greatly lessened.

The mere inclusion of gentian violet in a feed is not very effective as a mold inhibitor. The gentian violet particles are not in contact with every feed particle. The inclusion of equal amounts of gentian violet particles and feed particles would not really produce a good mold inhibitor.

The term inert ingredients as regards the animal or poultry feed, includes the normal feed ingredients but excludes materials which have a therapeutic or pharmacological activity. The term, more specifically, is medically-inert ingredients, and excludes any agent besides gentian violet which has a sparing effect for poultry and animals from the toxic and/or lethal effects of mycotoxins, such as, aflatoxins.

A vitamin mixture can be used as the carrier for the gentian violet in the premix used in this invention.

This invention is not intended for use in humans.

Gentian violet is not effective against aflatoxin production in feeds, i.e., it is not a mold inhibitor in feeds. Various chemicals, in gaseous or liquid form, have been applied to feeds to neutralize aflatoxin in such feeds. There are many problems with such chemicals. Gentian violet is used in a solid form, so it does not operate in that manner in the feed. Gentian violet, within the scope of this invention is present in feed which is consumed by the animal or poultry — the gentian violet spares the animal or poultry from the toxic effects of the aflatoxin in the consumed feed.

Herein all parts, ratios, proportions and percentages are on a weight basis, unless otherwise stated or obvious to one ordinarily skilled in the art.

The following examples illustrate this invention.

EXAMPLE 1

160 day-old chicks were randomly divided into sixteen groups of 10 chicks each. The chicks were hatch run and were all from the same breeder flocks. All of the chicks were wing banded and debeaked at one day of age. All of the chicks were MD vaccinated on day one and were NC-IB vaccinated during the experiment.

The feed was prepared by preparing 1,600 pounds of a 24 percent protein broiler mash. The 1,600 pounds of feed were divided into sixteen equal batches of 100 lbs. each. The sixteen groups of chicks received gentian violet and/or aflatoxin B-1 in the amounts set out in the following table:

TABLE 1

Checkerboard experimental design for groups of chicks to receive gentian violet (0, 7, 21 or 35 ppm) and B-1 aflatoxin (0, 1, 4 or 10 ppm) in their feed.

|  |  | Gentian Violet (ppm) | | | |
| --- | --- | --- | --- | --- | --- |
|  |  | 0 | 7 | 21 | 35 |
| B-1 Afla-toxin[b] | 0 | Gp 1[a] | Gp 2 | Gp 3 | Gp 4 |
|  | 1 | Gp 5 | Gp 6 | Gp 7 | Gp 8 |
|  | 4 | Gp 9 | Gp 10 | Gp 11 | Gp 12 |
|  | 10 | Gp 13 | Gp 14 | Gp 15 | Gp 16 |

Notes:
[a] 10 chicks per group
[b] 916.7 mg B-1 aflaxtoxin plus 9.167 gm feed equal stock toxin at 100 ppm VIGEN premix contained 1.55 percent of gentian violet, 1 percent of white mineral oil, 1.65 percent of Micro-Cel E, and 91.8 percent of corn cob fractions and 4 percent distilled water and was manufactured by A.H.P., Inc., of Gainesville, Ga. Enough VIGEN premix was used to achieve the desired gentian violet level desired in each of the sixteen feed batches. A sample (1 lb.) for each feed batch (lot) was set aside for future testing purposes. Feed remaining at termination of the trial (day 20) was weighed to determine the feed consumed by each group of birds.

The test was conducted for 20 days. The parameters measured during the test were: (1) weight gains — all of the groups vs. the controls — by pen at the conclusion of the trial; and (2) the sparing effect of gentian violet from the toxicity of B-1 aflatoxin.

Analysis of the chick weights at 20 days of age was done utilizing an analysis of variance (one-way with equal and unequal replications). The principal object in performing the analysis of variance was to be able to compare the mean weights by the method of least significant differences. (For this reason, whether the analysis of variance was significant or not is of no consequence in this study).

During the test, continued observation was made of mortality, feed consumption, diarrhea, etc. On the tenth day after the start of the test, the chickens were vaccinated NC-IB by treatment Broilerbron spray. The chickens were weighed on a day of age, 7, 14 and 20 days of age. The chicken weights (at 7, 14 and 20 days of age) are given in the following table:

Table 2

| | | Weight of Chickens | | |
| --- | --- | --- | --- | --- |
| | | Wt. at 7 days, gm. | Wt. at 14 days, gm. | Wt. at 20 days, gm. |
| Group No. 1 | | | | |
| Chicken No. | 1 | 111 | 251 | 468 |
| | 2 | 108 | 234 | 395 |
| | 3 | 126 | 249 | 395 |
| | 4 | 105 | 288 | 396 |
| | 5 | 90 | 211 | 459 |
| | 6 | 111 | 281 | 402 |
| | 7 | 118 | 262 | 367 |
| | 8 | 111 | 255 | 420 |
| | 9 | 111 | 248 | 433 |
| | 10 | 111 | 253 | 395 |
| Group No. 2 | | | | |
| Chicken No. | 1 | 126 | 264 | 418 |
| | 2 | 123 | 255 | 365 |
| | 3 | 133 | 278 | 444 |
| | 4 | 108 | 288 | 337 |
| | 5 | 98 | 277 | 416 |
| | 6 | 94 | 247 | 432 |
| | 7 | 125 | 270 | 455 |
| | 8 | 105 | 205 | 438 |
| | 9 | 114 | 177 | 420 |
| | 10 | 113 | 271 | 334 |
| Group No. 3 | | | | |
| Chicken No. | 1 | 122 | 252 | 407 |
| | 2 | 105 | 288 | 429 |
| | 3 | 120 | 243 | 416 |
| | 4 | 114 | 237 | 384 |
| | 5 | 116 | 276 | 409 |
| | 6 | 100 | 252 | 419 |
| | 7 | 98 | 238 | 396 |
| | 8 | 127 | 271 | 414 |
| | 9 | 109 | 226 | 397 |
| | 10 | 114 | 259 | 417 |
| Group No. 4 | | | | |
| Chicken No. | 1 | 120 | 303 | 419 |
| | 2 | 105 | 269 | 485 |
| | 3 | 127 | 242 | 422 |
| | 4 | 110 | 247 | 412 |
| | 5 | 124 | 222 | 438 |
| | 6 | 109 | 277 | 407 |
| | 7 | 116 | 269 | 362 |
| | 8 | 108 | 276 | 403 |
| | 9 | 95 | 255 | 334 |
| | 10 | 101 | 203 | 286 |
| Group No. 5 | | | | |
| Chicken No. | 1 | 114 | 272 | 436 |
| | 2 | 114 | 259 | 441 |
| | 3 | 109 | 259 | 373 |
| | 4 | 115 | 275 | 437 |
| | 5 | 117 | 268 | 413 |
| | 6 | 130 | 306 | 384 |
| | 7 | 112 | 258 | 417 |
| | 8 | 102 | 230 | 427 |
| | 9 | 121 | 247 | 501 |
| | 10 | 119 | 275 | 471 |
| Group No. 6 | | | | |
| Chicken No. | 1 | 119 | 242 | 435 |
| | 2 | 98 | 256 | 387 |
| | 3 | 118 | 248 | 395 |
| | 4 | 111 | 274 | 438 |
| | 5 | 118 | 224 | 398 |
| | 6 | 98 | 240 | 359 |
| | 7 | 118 | 239 | 409 |

Table 2-continued

| | | Wt. at 7 days, gm. | Wt. at 14 days, gm. | Wt. at 20 days, gm. |
|---|---|---|---|---|
| | 8 | 110 | 243 | 423 |
| | 9 | 108 | 273 | 393 |
| | 10 | 100 | 265 | 429 |
| Group No. 7 | | | | |
| Chicken No. | 1 | 87 | 237 | 398 |
| | 2 | 116 | 226 | 407 |
| | 3 | 109 | 258 | 392 |
| | 4 | 91 | 259 | 396 |
| | 5 | 114 | 278 | 387 |
| | 6 | 103 | 254 | 368 |
| | 7 | 107 | 257 | 408 |
| | 8 | 108 | 292 | 395 |
| | 9 | 117 | 243 | 375 |
| | 10 | 101 | 238 | 402 |
| Group No. 8 | | | | |
| Chicken No. | 1 | 100 | 255 | 373 |
| | 2 | 102 | 267 | 387 |
| | 3 | 104 | 269 | 399 |
| | 4 | 105 | 235 | 444 |
| | 5 | 101 | 258 | 437 |
| | 6 | 112 | 242 | 379 |
| | 7 | 104 | 233 | 458 |
| | 8 | 109 | 255 | 316 |
| | 9 | 99 | 241 | 401 |
| | 10 | 115 | 201 | 410 |
| Group No. 9 | | | | |
| Chicken No. | 1 | 99 | 202 | 285 |
| | 2 | 106 | 198 | 314 |
| | 3 | 105 | 202 | 206 |
| | 4 | 94 | 188 | 305 |
| | 5 | 107 | 179 | 187 |
| | 6 | 76 | 213 | 298 |
| | 7 | 99 | 141 | 246 |
| | 8 | 78 | 165 | 262 |
| | 9 | 88 | 125 | 235 |
| | 10 | 88 | 102 | — |
| Group No. 10 | | | | |
| Chicken No. | 1 | 105 | 208 | 294 |
| | 2 | 105 | 212 | 298 |
| | 3 | 116 | 259 | 397 |
| | 4 | 90 | 230 | 392 |
| | 5 | 88 | 218 | 329 |
| | 6 | 116 | 205 | 292 |
| | 7 | 112 | 235 | 221 |
| | 8 | 104 | 146 | 209 |
| | 9 | 103 | 165 | 323 |
| | 10 | 112 | 239 | 329 |
| Group No. 11 | | | | |
| Chicken No. | 1 | 114 | 275 | 291 |
| | 2 | 121 | 261 | 344 |
| | 3 | 112 | 256 | 404 |
| | 4 | 116 | 259 | 400 |
| | 5 | 105 | 218 | 251 |
| | 6 | 114 | 247 | 285 |
| | 7 | 109 | 191 | 362 |
| | 8 | 100 | 166 | 337 |
| | 9 | 90 | 185 | 393 |
| | 10 | 81 | — | 428 |
| Group No. 12 | | | | |
| Chicken No. | 1 | 88 | 218 | 344 |
| | 2 | 121 | 230 | 324 |
| | 3 | 122 | 191 | 252 |
| | 4 | 113 | 228 | 347 |
| | 5 | 122 | 193 | 303 |
| | 6 | 108 | 189 | 273 |
| | 7 | 97 | 163 | 290 |
| | 8 | 113 | 132 | 366 |
| | 9 | 99 | 216 | 298 |
| | 10 | 114 | 157 | 197 |
| Group No. 13 | | | | |
| Chicken No. | 1 | 86 | 182 | 208 |
| | 2 | 85 | 193 | 116 |
| | 3 | 93 | 164 | 235 |
| | 4 | 103 | 144 | 280 |
| | 5 | 97 | 121 | 219 |
| | 6 | 104 | 141 | 220 |
| | 7 | 78 | 153 | 104 |
| | 8 | 88 | 136 | 198 |
| | 9 | 97 | 77 | 189 |
| | 10 | 113 | — | — |
| Group No. 14 | | | | |
| Chicken No. | 1 | 101 | 167 | 249 |
| | 2 | 97 | 178 | 244 |
| | 3 | 94 | 142 | 232 |
| | 4 | 94 | 178 | 292 |
| | 5 | 89 | 189 | 196 |
| | 6 | 75 | 137 | 211 |
| | 7 | 102 | 158 | 189 |
| | 8 | 98 | 138 | 259 |
| | 9 | 94 | 129 | 180 |
| | 10 | 96 | — | — |
| Group No. 15 | | | | |
| Chicken No. | 1 | 104 | 210 | 248 |
| | 2 | 77 | 239 | 254 |
| | 3 | 97 | 164 | 311 |
| | 4 | 116 | 188 | 271 |
| | 5 | 103 | 161 | 229 |
| | 6 | 71 | 189 | 232 |
| | 7 | 100 | 162 | 241 |
| | 8 | 87 | 157 | — |
| | 9 | 98 | 84 | — |
| | 10 | — | — | — |
| Group No. 16 | | | | |
| Chicken No. | 1 | 90 | 158 | 243 |
| | 2 | 102 | 128 | 250 |
| | 3 | 90 | 193 | 198 |
| | 4 | 88 | 147 | 254 |
| | 5 | 91 | 147 | 224 |
| | 6 | 89 | 134 | 180 |
| | 7 | 96 | 129 | 217 |
| | 8 | 69 | 170 | 177 |
| | 9 | 83 | 146 | 182 |
| | 10 | 105 | 105 | 230 |

To address the question of the sparing effect of gentian violet in aflatoxin intoxication, four comparisons were made:

(1) The mean weight of the chicks receiving gentian violet but no B-1 aflatoxin.

These results and analysis are presented in Table 3. In this instance no significant difference was demonstrated between the mean weights of the chicks receiving either 0, 7, 21 or 35 ppm of genian violet in their feed.

TABLE 3

Control Groups. The weights of four groups of chicks (10 chicks per group) fed either 0, 7, 21 or 35 ppm gentian violet in their feed at 20 days of age.

| | Gentian Violet in The Feed | | | | Chicken No. In The Particular Group |
|---|---|---|---|---|---|
| | 0 ppm | 7 ppm | 21 ppm | 35 ppm | |
| weight, gm. | 468 | 418 | 407 | 419 | 1 |
| | 395 | 365 | 429 | 485 | 2 |
| | 395 | 444 | 416 | 422 | 3 |
| | 396 | 337 | 384 | 412 | 4 |
| | 459 | 416 | 409 | 438 | 5 |
| | 402 | 432 | 419 | 407 | 6 |
| | 367 | 455 | 396 | 362 | 7 |
| | 420 | 438 | 414 | 403 | 8 |
| | 433 | 420 | 397 | 334 | 9 |
| | 395 | 334 | 417 | 286 | 10 |
| $\bar{x}=$ | 413 | 405.9 | 408.8 | 396.8 | |
| n= | 10 | 10 | 10 | 10 | |

ANOVA

| Source of Variation | df | SS | MS | F |
|---|---|---|---|---|
| Treatments | 4−1=3 | 1414.2750 | 471.4250 | 0.2993 (NS) |
| Error | 36 | 56688.1 | 1574.6694 | |
| Total | 39 | 58102.375 | | | lsd (0.5) = t .05 Sd = 2.0336 × 17.7463 = 36.0889

Difference Between Mean Weights

| gentian violet (ppm) | | | |
|---|---|---|---|
| 35 | 7 | 21 | 0 |
| 396.8 | 405.9 | 408.8 | 413 (a) |

$(a)$ = any mean underscored by the same line is not significantly different at the 5% level of probability.

(2) The mean weights of chicks receiving B-1 aflatoxin at the 1 ppm level and gentian violet.

These results and analysis are given in Table 4. The mean weight of the birds receiving no gentian violet (weighing 430 gms) was not significantly different than the birds receiving gentian violet at the 7 ppm level (406.6). On the other hand gentian violet fed at either 7, 35 or 21 ppm did not result in any significant differences in the mean weights of the groups in question.

TABLE 4

Aflatoxin (1ppm). The weights of four groups of chicks (10 per group) all fed B-1 aflatoxin (1 ppm in feed) and either 0, 7, 21 or 35 ppm gentian violet in their feed at 20 days of age.

| | Gentian Violet in the Feed | | | | Chicken No. in the particular group |
|---|---|---|---|---|---|
| | 0 ppm | 7 ppm | 21 ppm | 35 ppm | |
| weight, gm. | 436 | 435 | 398 | 373 | 1 |
| | 441 | 387 | 407 | 387 | 2 |
| | 373 | 395 | 392 | 399 | 3 |
| | 437 | 438 | 396 | 444 | 4 |
| | 413 | 398 | 387 | 437 | 5 |
| | 384 | 359 | 368 | 379 | 6 |
| | 417 | 409 | 408 | 458 | 7 |
| | 427 | 423 | 395 | 316 | 8 |
| | 501 | 393 | 375 | 401 | 9 |
| | 471 | 429 | 402 | 410 | 10 |
| $\bar{x}$= | 430 | 406.6 | 392.8 | 400.4 | |
| n= | 10 | 10 | 10 | 10 | |

ANOVA

| Source of Variation | df | SS | MS | F |
|---|---|---|---|---|
| Treatments | 4−1=3 | 7735.5 | 2578.5 | 2.6474 (NS) |
| Error | 36 | 35062.4 | 973.9555 | |
| Total | 40−1=39 | 42797.9 | | | lsd (0.05) = t 0.05 sd = 2.0336 × 13.9567 = 28.3823

Difference Between Mean Weights

| Gentian Violet (ppm) | | | | |
|---|---|---|---|---|
| 21 | 35 | 7 | 0 | |
| 392.8 | 400.4 | 406.6 | 430 | (a) |

[a] = any mean underscored by the same line is not significantly different at the 5% level of probability (3) The mean weights of the chicks receiving B-1 aflatoxin at the 4 ppm level and gentian violet.

These results and analysis are given in Table 5. The mean weight of the birds receiving gentian violet at the 21 ppm level was significantly heavier (P>0.05) than the birds not receiving gentian violet (349.5 gms vs. 259.4 gms). In turn, there was no significant differences in the mean weights of the birds receiving gentian violet.

TABLE 5

Aflatoxin (4ppm). The weights of four groups of chicks (10 per group) all fed B-1 aflatoxin (4 ppm in feed) and either 0, 7, 21 or 35 ppm gentian violet in their feed at 20 days of age.

| | Gentian Violet in the Feed | | | | Chicken No. in the particular group |
|---|---|---|---|---|---|
| | 0 ppm | 7 ppm | 21 ppm | 35 ppm | |
| weight, gm. | 285 | 294 | 291 | 344 | 1 |
| | 314 | 298 | 344 | 324 | 2 |
| | 206 | 397 | 404 | 252 | 3 |
| | 305 | 392 | 400 | 347 | 4 |
| | 187 | 329 | 251 | 303 | 5 |
| | 298 | 292 | 285 | 273 | 6 |
| | 246 | 221 | 362 | 290 | 7 |
| | 262 | 209 | 337 | 366 | 8 |
| | 235 | 323 | 393 | 298 | 9 |
| | — | 329 | 428 | 197 | 10 |
| $\bar{x}$= | 259.8 | 308.4 | 349.5 | 299.4 | |

TABLE 5-continued

Aflatoxin (4ppm). The weights of four groups of chicks (10 per group) all fed B-1 aflatoxin (4 ppm in feed) and either 0, 7, 21 or 35 ppm gentian violet in their feed at 20 days of age.

| n=9 | 10 | 10 | 10 |
|---|---|---|---|

ANOVA

| Source of Variation | df | SS | MS | F |
|---|---|---|---|---|
| Treatments | 4−1=3 | 38630.5803 | 12876.8601 | 4.387 * |
| Error | 35 | 104114.8556 | 2974.7101 | |
| Total | 39−1=38 | 142745.4359 | | | lsd (0.05) = t 0.05 (35) Sd = 2.2205 × 25.0591 = 55.6437[a]
= 2.2205 × 24.3914 = 54.1611

Gentian Violet (ppm)

| 0 | 35 | 7 | 21 | |
|---|---|---|---|---|
| 259.4 | 299.4 | 308.4 | 349.5 | (b) |

[a] = for any comparison involving 9 replicates (Gentian Violet 0 ppm)
[b] = any mean underscored by the same line is not significantly different at the 5% level of probability (4) The mean weights of the chicks receiving B-1 aflatoxin at the 10 ppm level and gentian violet.

These results and analysis are presented in Table 6. Again, the mean weight of the group of chicks receiving gentian violet at the 21 ppm level was significantly larger than the group not receiving gentian violet (P>0.05). There were no significant differences in the mean weights of the chicks receiving gentian violet at any level.

TABLE 6

Aflatoxin (10 ppm). The weights of four groups of chicks (10 per group) all fed B-1 aflatoxin (10 ppm in feed) and either 0, 7, 21 or 35 ppm gentian violet in their feed at 20 days of age.

| | Gentian Violet in the Feed | | | | Chicken No. in the particular group |
|---|---|---|---|---|---|
| | 0 ppm | 7 ppm | 21 ppm | 35 ppm | |
| weight, gm. | 208 | 249 | 248 | 243 | 1 |
| | 116 | 244 | 254 | 250 | 2 |
| | 235 | 232 | 311 | 198 | 3 |
| | 280 | 292 | 271 | 254 | 4 |
| | 219 | 196 | 229 | 224 | 5 |
| | 220 | 211 | 232 | 180 | 6 |
| | 104 | 189 | 241 | 217 | 7 |
| | 198 | 259 | — | 177 | 8 |
| | 189 | 180 | — | 182 | 9 |
| | — | — | — | 230 | 10 |
| $\bar{x}$ = | 196.6 | 228 | 255.1 | 215.5 | |
| n = | 9 | 9 | 7 | 10 | |

ANOVA

| Source of Variation | df | SS | MS | F |
|---|---|---|---|---|
| Treatments | 4 − 1 = 3 | 14260.5920 | 4753.5306 | 3.0461 (NS) |
| Error | 31 | 48375.5795 | 1560.5025 | |
| Total | 35 − 1 = 34 | | | | lsd(0.05) = t.05(31)Sd = 2.0399 × 18.1499 = 37.0240[a]
= 2.0399 × 19.6803 = 40.1458
= 2.0399 × 18.6210 = 37.9850
= 2.0399 × 19.9050 = 40.6042

Difference Between Mean Weights

| Gentian Violet (ppm) | | | | |
|---|---|---|---|---|
| 0 | 35 | 7 | 21 | |
| 196.6 | 215.5 | 228 | 255.1 | (b) |

[a] = for comparisons involving n's of 10 and 9, 10 and 7, 9 and 9, 9 and 7, respectively
[b] = any mean underscored by the same line is not significantly different at the 5%

The deleterious effects of aflatoxin is well illustrated by Tables 7, 8, 9 and 10. In this instance the effects of B-1 aflatoxin was observed within the groups of chicks receiving gentain violet at the 0, 7, 21 and 35 ppm dosage levels. In every instance there was no significant difference (P< =0.05) in the mean weights of the groups of chicks receiving either 0 or 1 ppm B-1 aflatoxin. However, in every case the mean weights of the groups of chicks receiving 0 or 1 ppm aflatoxin was significantly larger than the groups of chicks receiving 4 ppm (P>0.05). In turn, the mean weights of groups receiving 4 ppm was significantly heavier than the mean weights of the groups receiving 10 ppm.

TABLE 7

Gentian Violet (0 ppm). The weights of four groups of chicks (10 per group) all fed B-1 aflatoxin in their feed at either 0, 1, 4 or 10 ppm at 20 days of age.

| | B-1 Aflatoxin In the Feed | | | | Chicken No. in the particular group |
|---|---|---|---|---|---|
| | 0 ppm | 1 ppm | 4 ppm | 10 ppm | |
| weight, gm. | 468 | 436 | 285 | 208 | 1 |
| | 395 | 441 | 314 | 116 | 2 |
| | 395 | 373 | 206 | 235 | 3 |
| | 396 | 437 | 305 | 280 | 4 |
| | 459 | 413 | 187 | 219 | 5 |
| | 402 | 384 | 298 | 220 | 6 |
| | 367 | 417 | 246 | 104 | 7 |
| | 420 | 427 | 262 | 198 | 8 |
| | 433 | 501 | 235 | 189 | 9 |
| | 395 | 471 | — | — | 10 |
| $\bar{x}$ = | 413 | 430 | 259.8 | 196.6 | |
| n = | 10 | 10 | 9 | 9 | |

ANOVA

| Source of Variation | df | SS | MS | F |
|---|---|---|---|---|
| Treatment | 4 − 1 = 3 | 373536.9853 | 124512.3284 | 67.5533[a] |
| Error | = 34 | 62667.7779 | 1843.1699 | |
| Total | 38 − 1 = 37 | 436204.7632 | | |

$$a = P > 0.005$$
$$\text{lsd}(0.05) = t.05(34)S\bar{d} = 2.0336 \times 19.1998 = 39.0447^{(b)}$$
$$= 2.0336 \times 19.7254 = 40.1136^{(c)}$$
$$= 2.0336 \times 20.2374 = 41.1548^{(d)}$$

Difference in Mean Weights

| B-1 Aflatoxin (ppm) | | | |
|---|---|---|---|
| 10 | 4 | 0 | 1 |
| 196.6 | 259.8 | 413 | 430 | (e)

[b] = for comparisons involving 10 replicates in each mean
[c] = for comparisons involving 10 replicates in one mean and 9 in the other
[d] = for comparisons involving 9 replicates in each mean
[e] = any means underscored by the same line are not significantly different at the 5% level of probability

TABLE 8

Gentian Violet (7 ppm). The weights of four groups of chicks (10 per group) all fed gentian violet 7ppm (feed) and B-1 aflatoxin in their feed at either 0, 1, 4 or 10 ppm at 20 days of age.

| | B-1 Aflatoxin In the Feed | | | | Chicken No. in the particular group |
|---|---|---|---|---|---|
| | 0 ppm | 1 ppm | 4 ppm | 10 ppm | |
| weight, gm. | 418 | 435 | 294 | 249 | 1 |
| | 365 | 387 | 298 | 244 | 2 |
| | 444 | 395 | 397 | 232 | 3 |
| | 337 | 438 | 392 | 292 | 4 |
| | 416 | 398 | 329 | 196 | 5 |
| | 432 | 359 | 292 | 211 | 6 |
| | 455 | 409 | 221 | 189 | 7 |
| | 438 | 423 | 209 | 259 | 8 |
| | 420 | 393 | 323 | 180 | 9 |
| | 334 | 429 | 329 | — | 10 |
| $\bar{x}$ = | 405.9 | 406.6 | 308.4 | 228 | |
| n = | 10 | 10 | 10 | 9 | |

| Source of Variation | df | SS | MS | F |
|---|---|---|---|---|
| Treatments | 4 − 1 = 3 | 210,665.2744 | 70,221.7581 | 36.0715[a] |
| Error | 35 | 68,135.7 | 1946.7342 | |
| Total | 39 − 1 = 38 | 278,800.9744 | | |

TABLE 8-continued

Gentian Violet (7 ppm). The weights of four groups of chicks (10 per group) all fed gentian violet 7ppm (feed) and B-1 aflatoxin in their feed at either 0, 1, 4 or 10 ppm at 20 days of age.

$$(a) = P > 0.005$$
$$\text{lsd}(0.05) = t.05(35)S\bar{d} = 2.0315 \times 19.7318 = 40.0852^{(b)}$$
$$= 2.0315 \times 20.2720 = 41.1826^{(c)}$$

$$^{(b)} = \frac{n}{10 + 10} S\bar{d} = \sqrt{1946.7342 \left(\frac{1}{10} + \frac{1}{10}\right)} = 19.7318$$

$$^{(c)} = 10 + 9 S\bar{d}\,^{v} \sqrt{1946.7342 \left(\frac{1}{10} + \frac{1}{9}\right)} = 20.2720$$

Difference in Mean Weights

| B-1 Aflatoxin (ppm) | | | |
|---|---|---|---|
| 10 | 4 | 0 | 1 |
| 228 | 308.4 | 405.9 | 406.6 | (d)

[d] = any means underscored by the same line are not significantly different at the 5% level of probability

TABLE 9

Gentian violet (21 ppm). The weights of four groups of chicks (10 per group) all fed gentian violet 21 ppm (feed) and B-1 aflatoxin in their feed at either 0, 1, 4 or 10 ppm at 20 days of age.

| | B-1-Aflatoxin | | | | Chicken No. in the particular group |
|---|---|---|---|---|---|
| | 0 ppm | 1 ppm | 4 ppm | 10 ppm | |
| weight, gm. | 407 | 398 | 291 | 248 | 1 |
| | 429 | 407 | 344 | 254 | 2 |
| | 416 | 392 | 404 | 311 | 3 |
| | 384 | 396 | 400 | 271 | 4 |
| | 409 | 387 | 251 | 229 | 5 |
| | 419 | 368 | 285 | 232 | 6 |
| | 396 | 408 | 362 | 241 | 7 |
| | 414 | 395 | 337 | — | 8 |
| | 397 | 375 | 393 | — | 9 |
| | 417 | 402 | 428 | — | 10 |
| $\bar{x}$ = | 408.8 | 392.8 | 349.5 | 255.1 | |
| n = | 10 | 10 | 10 | 7 | |

ANOVA

| Source of Variation | df | SS | MS | F |
|---|---|---|---|---|
| Treatments | 4−1=3 | 112,626.1456 | 37,542.0485 | 31.6441[a] |
| Error | 33 | 39,150.5572 | 1,186.3805 | |
| Total | 37−1=36 | 151,776.7028 | | |

$$(a) = P > 0.005$$
$$\text{lsd}(0.05) = t.05S\bar{d} = 2.0357 \times 15.4037 = 31.3573^{(b)}$$
$$= 2.0357 \times 16.9721 = 34.5501^{(c)}$$

$$^{(b)} = \frac{n}{10} + 10\, S\bar{d} = \sqrt{1,186.3805 \left(\frac{1}{10} + \frac{1}{10}\right)} = 15.4037$$

$$^{(c)} = 10 + 7\, S\bar{d} = \sqrt{1,186.3805 \left(\frac{1}{7} + \frac{1}{10}\right)} = 16.9721$$

Difference in Mean Weights

| B-1 aflatoxin (ppm) | | | |
|---|---|---|---|
| 10 | 4 | 1 | 0 |
| 255.1 | 349.5 | 392.8 | 408.8 | (d)

[d] = any means underscored by the same line are not significantly different at the 5% level of significance

TABLE 10

Gentian violet (35 ppm). The weights of four groups of chicks (10 per group) all fed gentian violet 35 ppm (feed) and B-1 aflatoxin in their feed at either 0, 1, 4 or 10 ppm at 20 days of age.

| | B-1 Aflatoxin In the Feed | | | | Chicken No. in the particular group |
|---|---|---|---|---|---|
| | 0 ppm | 1 ppm | 4 ppm | 10 ppm | |
| weight, gm. | 419 | 373 | 344 | 243 | 1 |
| | 485 | 387 | 324 | 250 | 2 |

TABLE 10-continued

Gentian violet (35 ppm).
The weights of four groups of
chicks (10 per group) all fed gentian violet 35 ppm
(feed) and B-1 aflatoxin in their feed at either
0, 1, 4 or 10 ppm at 20 days of age.

| 422 | 399 | 252 | 198 | 3 |
|---|---|---|---|---|
| 412 | 444 | 347 | 254 | 4 |
| 438 | 437 | 303 | 224 | 5 |
| 407 | 379 | 273 | 180 | 6 |
| 362 | 458 | 290 | 217 | 7 |
| 403 | 316 | 366 | 177 | 8 |
| 334 | 401 | 298 | 182 | 9 |
| 286 | 410 | 197 | 230 | 10 |
| $\bar{x}$ = 396.8 | 400.4 | 299.4 | 215.5 | |
| n = 10 | 10 | 10 | 10 | |

ANOVA

| Source of Variation | df | SS | MS | F |
|---|---|---|---|---|
| Treatment | 4−1=3 | 234,494.0750 | 78,164.6916 | 37.8792[a] |
| Error | 36 | 74,286.9 | 2,063.5250 | |
| Total | 40−1=39 | | | |

[a] = P>0.005 lsd(0.05) = t.05(36)S$\bar{d}$ = 2.0294 × 20.3151 = 41.2275

S$\bar{d}$ = $\sqrt{2(2063.5250)/10}$ = 20.3151

Difference in Mean Weights
B-1 Aflatoxin (ppm)

| 10 | 4 | 0 | 1 |
|---|---|---|---|
| 215.5 | 299.4 | 396.8 | 400.4 |

[b]

[b] = any two means underscored by the same line are not significantly different at the 5% level of probability When B-1 aflatoxin was fed at the 0 to 1 ppm level, the gentian violet did not appear to have any effect on the mean weights of chicks at 20 days of age. When B-1 aflatoxin was fed at the 4 ppm level, gentian violet began to show a sparing effect in that the mean weight of the group of chicks receiving 21 ppm gentian violet (349.5 gms) was significantly larger (P>0.05) than the chicks receiving no gentian violet (259.4 gms). This is also true when B-1 aflatoxin was fed at the 10 ppm level. The reason that sparing effect was not evident until the B-1 aflatoxin is fed in 4 to 10 ppm is that these are the levels at which intoxication becomes manifest.

The sparing effect of gentian violet in the presence of intoxicating levels of B-1 aflatoxin apparently assumes a sigmoid curve. The dosage of 21 ppm appears on the linear part of this curve and appears to be the "best" dosage. The dosages of 7 and 35 ppm are at either extreme of the sigmoid curve. At this stage (20 days of age) no significant differences are in evidence between the mean wieghts of the 7, 21, and 35 ppm levels. However, a trend is evident at 20 days of age — see Example 2 for the significant differences that developed as the test was continued.

The gentian violet was not toxic even at the 35 ppm level in the feed.

It can be concluded that groups of chicks receiving 21 ppm gentian violet were significantly heavier than the groups not receiving gentian violet when they were fed B-1 aflatoxin at intoxicating levels (4 or 10 ppm in the feed).

EXAMPLE 2

Example 1 was continued, in part, for an additional three weeks (for a test duration of six weeks). The groups held beyond three weeks of age were controls, 21 ppm of gentian violet, 4 ppm of aflatoxin and 21 ppm of gentian violet with 4 ppm of aflatoxin. All other groups were terminated since 1 ppm of aflatoxin gave no apparent effect and 10 ppm of aflatoxin produced excessive effects. The 21 ppm of gentian violet was selected on the basis of results at 3 weeks of age.

TABLE 11

| | wt. at 4 wk., gm. | wt. at 5 wk., gm. | wt. at 6 wk., gm. |
|---|---|---|---|
| Group No. 1 | | | |
| Chicken No. 1 | 680 | 735 | 964 |
| 2 | 590 | 744 | 1021 |
| 3 | 495 | 774 | 872 |
| 4 | 604 | 812 | 1044 |
| 5 | 568 | 665 | 992 |
| 6 | 630 | 646 | 1043 |
| 7 | 592 | 750 | 959 |
| 8 | 575 | 770 | 858 |
| 9 | 583 | 833 | 864 |
| 10 | 616 | 868 | 996 |
| Ave wt. : | 5933 | 759.7 | 961.3 |
| Group No. 9 (4 ppm of aflatoxin) | | | |
| Chicken No. 1 | 270 | 348 | 697 |
| 2 | 420 | 400 | 518 |
| 3 | 315 | 413 | 782 |
| 4 | 391 | 512 | 533 |
| 5 | 175 | 259 | 704 |
| 6 | 430 | 570 | 716 |
| 7 | 500 | 582 | 527 |
| 8 | 400 | 552 | 934 |
| 9 | 325 | 714 | 398 |
| 10 | — | — | — |
| Ave. wt. : (based on 9 birds) | 358.4 | 483.3 | 645.4 |
| Group No. 3 (21 ppm of gentian violet) | | | |
| Chicken No. 1 | 610 | 753 | 1050 |
| 2 | 643 | 795 | 1065 |
| 3 | 673 | 878 | 994 |
| 4 | 572 | 800 | 1052 |
| 5 | 666 | 828 | 1004 |
| 6 | 630 | 834 | 1070 |
| 7 | 610 | 800 | 1031 |
| 8 | 613 | 825 | 969 |
| 9 | 594 | 786 | 955 |
| 10 | — | — | — |
| Ave wt. : | 623.4 | 811.0 | 1021.1 |
| Group No. 11 (4 ppm of aflatoxin and 21 ppm of gentian violet) | | | |
| Chicken No. 1 | 566 | 670 | 768 |
| 2 | 425 | 722 | 803 |
| 3 | 423 | 487 | 796 |
| 4 | 550 | 587 | 773 |
| 5 | 376 | 592 | 740 |
| 6 | 466 | 565 | 887 |
| 7 | 387 | 636 | 726 |
| 8 | 450 | 618 | 648 |
| 9 | — | — | — |
| 10 | — | — | — |
| Ave wt. : (based on 8 birds) | 455.4 | 609.6 | 767.6 |

By way of review, this example is an extension of Example 1 where the question was asked if gentian violet caused a sparing effect from the toxicity of B-1 aflatoxin in broiler chicks. In that experiment, which was terminated at 21 days of age, it was established that VIGEN did indeed cause a sparing effect. Further, it was established that the dose of aflatoxin delivered in the feed was critical in that 1 PPM had little effect on weight production and that 10 PPM was overwhelming. It was also observed that the best treatment dosage of gentian violet was about 21 PPM.

To determine if gentian violet continued to cause a sparing effect from the toxicity of aflatoxin, the Example 1 was continued until the broiler chickens were 6 weeks of age in selected groups.

This example is a continuation of Example 1 in four selected groups of broiler chickens. These groups are:

Group 1: Control. These birds were not given gentian violet or aflatoxin in their feed.

Group 3: 21 PPM of gentian violet. These birds were being given gentian violet at the rate of 21 PPM daily in their feed.

Group 9: 4 PPM B-1 of aflatoxin. These birds were being daily poisoned with aflatoxin being given at the dosage level of 4 PPM in their feed.

Group 11: 4 PPM B-1 of aflatoxin and 21 PPM of gentian violet. These birds were receiving both aflatoxin and gentian violet daily in their feed at the rates indicated.

Initially, at one-day of age, each group of birds contained 10 chicks each. There was normal chick attrition and at the start of this example, Group 1 had 10 chicks, Groups 3 and 9 had 9 chicks each, and Group 11 had 8 chicks. At the start of this trial, the birds were 3 weeks of age. The broiler chickens were weighed individually at 4, 5, and 6 weeks of age to the nearest gram.

The hypothesis proposed was that gentian violet does not have a sparing effect on broiler chicks when they are being poisoned with 4 PPM aflatoxin. Whether there is a sparing effect or not was judged on the basis of weight.

Analysis of the weight data was done utilizing an analysis of variance (one-way with unequal replication). The desired end was to compare the mean weights of the four groups of chicks by the method of least significant difference.

The weights of the broiler chickens at 4, 5 and 6 weeks of age are given in Tables 12, 13 and 14 respectively. Subsequent analysis of this data to compare the mean weight of each group to the mean weight of every other group is given in Table 15.

Table 12

Individual Weights[a] (gms) of Birds Receiving Either 4 PPM aflatoxin, 21 PPM gentian violet, 4 PPM aflatoxin and 21 PPM gentian violet, or a Control at 4 weeks of Age.

| Control | 4 PPM Aflatoxin | 21 PPM Gentian Violet | 4 PPM Aflafoxin & 21 PPM Gentian Violet |
|---|---|---|---|
| 680 | 270 | 610 | 566 |
| 590 | 420 | 643 | 425 |
| 495 | 315 | 673 | 423 |
| 604 | 391 | 572 | 550 |
| 568 | 175 | 666 | 376 |
| 630 | 430 | 630 | 466 |
| 592 | 500 | 610 | 387 |
| 575 | 400 | 613 | 450 |
| 583 | 325 | 594 | |
| 616 | | | |
| n = 0 | 9 | 9 | 8 |
| mean = 593.3 | 358.4 | 623.4 | 455.4 |

[a]Each group of birds initially contained 10 birds; 4 birds died for reasons not pertenant to the experiment.

Table 13

Individual Weights (gms) of Birds Receiving either 4 PPM aflatoxin, 21 PPM gentian violet, 4 PPM aflatoxin & 21 PPM gentian violet, or acting as a Control at 5 Weeks of Age.

| Control | 4 PPM aflatoxin | Gentian Violet | 4 PPM aflatoxin & 21 PPM Gentian |
|---|---|---|---|
| 735 | 348 | 753 | 670 |
| 744 | 400 | 795 | 722 |
| 774 | 413 | 878 | 487 |
| 812 | 512 | 800 | 587 |
| 665 | 259 | 834 | 565 |
| 646 | 570 | 800 | 636 |

Table 13-continued

Individual Weights (gms) of Birds Receiving either 4 PPM aflatoxin, 21 PPM gentian violet, 4 PPM aflatoxin & 21 PPM gentian violet, or acting as a Control at 5 Weeks of Age.

| Control | 4 PPM aflatoxin | Gentian Violet | 4 PPM aflatoxin & 21 PPM Gentian |
|---|---|---|---|
| 750 | 582 | 825 | 618 |
| 770 | 552 | 786 | |
| 833 | 714 | 786 | |
| 868 | | | |
| n = 10 | 9 | 9 | 8 |
| mean = 759.7 | 483.3 | 811.0 | 609.6 |

Table 14

Individual Weights (gms) of Birds Receiving 4 PPM aflatoxin, 21 PPM gentian violet, 4 PPM aflatoxin 21 PPM gentian violet, or acting as a Control at 6 Weeks of Age.

| Control | 4 PPM aflatoxin | 21 PPM Gentian Violet | 4 PPM aflatoxin & 21 PPM Gentian Violet |
|---|---|---|---|
| 964 | 697 | 1050 | 768 |
| 1021 | 518 | 1065 | 303 |
| 872 | 782 | 994 | 796 |
| 1044 | 533 | 1052 | 773 |
| 992 | 704 | 1004 | 740 |
| 1043 | 716 | 1070 | 887 |
| 959 | 527 | 1031 | 726 |
| 858 | 934 | 969 | 648 |
| 864 | 398 | 955 | |
| 996 | | | |
| n = 10 | 9 | 9 | 8 |
| mean = 961.3 | 645.44 | 1021.11 | 767.62 |

Table 15

Comparison of the mean weights of broiler chickens receiving in their feed either 4 PPM aflatoxin, 21 PPM gentian violet, 4 PPM aflatoxin & 21 PPM gentian violet, or a control by the method of least significant difference at 4, 5 and 6 Weeks of Age.

| | Mean Weights of Group (gms) | | | |
|---|---|---|---|---|
| Age | 4 PPM aflatoxin | 4 PPM aflatoxin & 21 PPM Gentian Violet | Control | 21 PPM Gentian Violet |
| 4 weeks | 358.4 | 455.4 | 593.3 | 623.4 [a] |
| 5 weeks | 483.3 | 609.6 | 759.7 | 811.0 |
| 6 weeks | 645.4 | 767.6 | 961.3 | 1021.1 |

[a]any mean underscored by the same line is not significantly different at the 5% level of probability In every instance the comparison of the mean weight of the group receiving 4 PPM of aflatoxin to the group receiving 4 PPM of aflatoxin and 21 PPM of gentian violet demonstrated the group receiving gentian violet was significantly heavier (P>0.05). For example:

| Age | aflatoxin Group Weight in gms | aflatoxin and gentian violet Group Weight in gms | Difference | Significant or Not |
|---|---|---|---|---|
| 4 | 358.4 | 455.4 | 97.0 | yes |
| 5 | 483.3 | 609.6 | 126.3 | yes |
| 6 | 645.4 | 767.6 | 122.2 | yes |

At the three age levels examined in this study, the mean weights of the control group was not significantly different than the group of birds receiving 21 PPM of gentian violet in their feed. Both of these groups have mean weights significantly heavier than the birds receiving 4 PPM aflatoxin and 21 PPM of gentian violet.

Since the group of birds receiving 4 PPM of aflatoxin and 21 PPM of gentian violet weighed significantly more than the group of broiler chickens being poisoned with 4 PPM of aflatoxin, the hypothesis that gentian vilet does not cause a sparing effect in broiler chickens being poisoned with aflatoxin must be rejected. Instead, the alternate hypothesis that gentian violet causes a sparing effect in broiler chickens when they are being poisoned with aflatoxin has to be accepted.

At ages 4, 5 and 6 weeks, the group of birds receiving 21 PPM of gentian violet in their feed had mean weights 30.1, 51.3 and 59.8 gms heavier than their control counterparts. These differences, because of the small number of experimental units, are not significant. However, in this and other experiments, the trend for birds to gain weight faster than their control counterparts is patent.

EXAMPLE 3

Example 1 was repeated, using the following parameters:
- Secured 160 day-old broiler pullets
- Divided into 16 groups of 10 each
- Aflatoxin used at levels of 0, 1, 4 and 10 PPM
- Gentian violet used at levels of 0, 7, 21 and 35 PPM
- Broiler feed mixed to contain 24% protein
- Prepared 70 pounds of feed at each level of gentian violet
- Mixed 916.7 mg of B-1 Aflatoxin with 9,167 gm of feed to provide stock toxin at 100 PPM.
- Added: 700 gm toxin stock to 6,300 gm feed - 10 PPM
  280 gm toxin stock to 6,720 gm feed - 4 PPM
  70 gm toxin stock to 6,930 gm feed - 1 PPM
- These amounts added to feed with 0, 7, 21 and 35 PPM of gentian violet to provide the 16 combination of toxin and gentian violet.

Chicks were weighed at day-old, 7, 14 and 20 days of age with the results given on Table No. 16.

Hematocrits at 20 days were within the normal range in all groups with averages ranging from 28.9 to 36.5. There was no pattern to indicate any marked effect by level of either the aflatoxin or gentian violet. Blood clotting times (CT) were secured on all groups receiving 0 or 7 PPM of gentian violet. Untreated controls (0 toxin - 0 gentian violet) had average CT of 1.5 minutes. All others had longer CT with many over 5 minutes. However, there was marked variation both within and between groups and were too erratic to allow interpretation. The capillary tube method gives an indication of clotting time but a better method is needed before conclusive results can be obtained. It was generally observed, however, that the clotting times were quite long and a few birds bled to death from the wing vein puncture.

Feed conversions were calculated. The 4 and 10 PPM of aflatoxin had much poorer feed conversion and 1 PPM had little effect. Addition of gentian violet at 7 PPM improved feed conversion only with 1 PPM of aflatoxin. However, at 21 PPM of gentian violet and 4 PPM aflatoxin, there was marked improvement in feed conversion as well as weight gain.

Groups receiving 0 and 4 PPM of aflatoxin with 0, 7 and 21 PPM of gentian violet were being continued to 6 weeks of age. All other groups, 0 toxin - 35 of gentian violet, 4 toxin - 35 of gentian violet and 1 and 10 of toxin with 0, 7, 21 and 35 were necropsied. The 1 PPM of toxin produced slight subcutaneous hemorrhage with 0, 7 or 21 PPM of gentian violet but little or no liver or kidney changes. However, 10 PPM of aflatoxin caused considerable hemorrhage and marked liver and kidney changes with all levels (0, 7 and 21 PPM) of gentian violet. Changes were also evident at 4 and 10 PPM toxin with 35 PPM of gentian violet.

Table 16

| GENTIAN VIOLET WITH AFLATOXIN | | | | |
|---|---|---|---|---|
| Chick Weights in Grams | | | | |
| Gentian Violet PPM in Feed | | | | |
| | 0 | 7 | 21 | 35 |
| 0 | 39* | 39 | 38 | 38 |
| | 110 | 114 | 112 | 112 |
| | 253 | 253 | 254 | 256 |
| | 413 | 406 | 412 | 397 |
| 1 | 38 | 39 | 37 | 37 |
| Aflatoxin | 115 | 110 | 115 | 95 |
| PPM in feed | 265 | 248 | 254 | 192 |
| | 430 | 407 | 393 | 400 |
| 4 | 38 | 38 | 39 | 38 |
| | 94 | 105 | 106 | 110 |
| | 172 | 212 | 229 | 192 |
| | 260 | 308 | 350 | 299 |
| 10 | 38 | 37 | 38 | 37 |
| | 94 | 94 | 95 | 91 |
| | 146 | 157 | 173 | 146 |
| | 197 | 205 | 255 | 216 |

*Wt. in gms at day-old
7 days
14 days
20 days

EXAMPLE 4

Example 1 was repeated, except that lower aflatoxin levels and gentian violet were used at 7, 14 and 21 PPM. The sixteen groups of chicks received gentian violet and/or aflatoxin B-1 in the amounts set out in the following table:

Table 17

| Checkerboard experimental design for groups of chicks to receive gentian violet (0, 7, 14 or 21 PPM) and B-1 aflatoxin (0, 1, 2 or 3 PPM) in their feed. | | | | |
|---|---|---|---|---|
| | | Gentian Violet (PPM) | | |
| | 0 | 7 | 14 | 21 |
| 0 | Gp 1[a] | Gp 5 | Gp 9 | Gp 13 |
| 1 | Gp 2 | Gp 6 | Gp 10 | Gp 14 |
| B-1 2 | Gp 3 | Gp 7 | Gp 11 | Gp 15 |
| Aflatoxin 3 | Gp 4 | Gp 8 | Gp 12 | Gp 16 |

Notes:
[a] 15 chicks per group

The chicken weights are given in the following table:

TABLE 18

| WEIGHT OF CHICKENS | | | |
|---|---|---|---|
| | wt. at 7 days, gm. | wt. at 14 days, gm. | wt. at 21 days, gm. |
| Group No. 1 | | | |
| Chicken No. 1 | 121 | 257 | 485 |
| 2 | 116 | 226 | 423 |
| 3 | 119 | 247 | 357 |
| 4 | 114 | 262 | 365 |
| 5 | 109 | 229 | 354 |
| 6 | 110 | 247 | 428 |
| 7 | 119 | 294 | 350 |
| 8 | 131 | 198 | 377 |
| 9 | 112 | 268 | 392 |
| 10 | 112 | 239 | 442 |
| 11 | 114 | 230 | 456 |
| 12 | 98 | 218 | 388 |
| 13 | 105 | 288 | 326 |
| 14 | 108 | 222 | 413 |
| 15 | 92 | 195 | 334 |
| Group No. 2 | | | |
| Chicken No. 1 | 111 | 255 | 394 |
| 2 | 136 | 255 | 483 |
| 3 | 118 | 232 | 406 |
| 4 | 111 | 311 | 469 |
| 5 | 113 | 247 | 413 |
| 6 | 130 | 309 | 349 |
| 7 | 103 | 281 | 375 |

TABLE 18-continued
WEIGHT OF CHICKENS

| | wt. at 7 days, gm. | wt. at 14 days, gm. | wt. at 21 days, gm. |
|---|---|---|---|
| 8 | 104 | 238 | 360 |
| 9 | 108 | 268 | 402 |
| 10 | 103 | 231 | 458 |
| 11 | 136 | 230 | 351 |
| 12 | 123 | 258 | 400 |
| 13 | 116 | 237 | 361 |
| 14 | 108 | 226 | 397 |
| 15 | 124 | 256 | 380 |
| Group No. 3 | | | |
| Chicken No. 1 | 131 | 241 | 424 |
| 2 | 113 | 242 | 392 |
| 3 | 104 | 241 | 421 |
| 4 | 107 | 244 | 473 |
| 5 | 81 | 212 | 368 |
| 6 | 115 | 216 | 417 |
| 7 | 106 | 244 | 448 |
| 8 | 126 | 276 | 409 |
| 9 | 121 | 219 | 366 |
| 10 | 118 | 245 | 318 |
| 11 | 102 | 223 | 332 |
| 12 | 110 | 184 | 369 |
| 13 | 126 | 223 | 357 |
| 14 | 112 | 251 | 316 |
| 15 | 116 | 199 | 332 |
| Group No. 4 | | | |
| Chicken No. 1 | 115 | 210 | 393 |
| 2 | 114 | 231 | 372 |
| 3 | 49 | 186 | 330 |
| 4 | 85 | 152 | 396 |
| 5 | 112 | 253 | 325 |
| 6 | 112 | 208 | 371 |
| 7 | 112 | 224 | 271 |
| 8 | 123 | 221 | 417 |
| 9 | 113 | 198 | 362 |
| 10 | 114 | 230 | 555 |
| 11 | 104 | 188 | 337 |
| 12 | 110 | 270 | 293 |
| 13 | 125 | 206 | 333 |
| 14 | 92 | 207 | 205 |
| 15 | — | — | — |
| Group No. 5 | | | |
| Chicken No. 1 | 81 | 227 | 496 |
| 2 | 79 | 248 | 403 |
| 3 | 120 | 212 | 425 |
| 4 | 115 | 232 | 443 |
| 5 | 123 | 258 | 396 |
| 6 | 106 | 287 | 300 |
| 7 | 102 | 261 | 371 |
| 8 | 103 | 229 | 423 |
| 9 | 122 | 215 | 416 |
| 10 | 106 | 196 | 328 |
| 11 | 112 | 228 | 364 |
| 12 | 100 | 239 | 277 |
| 13 | 134 | 238 | 381 |
| 14 | 101 | 204 | 342 |
| 15 | 94 | 160 | 396 |
| Group No. 6 | | | |
| Chicken No. 1 | 124 | 260 | 409 |
| 2 | 116 | 158 | 384 |
| 3 | 109 | 267 | 442 |
| 4 | 125 | 248 | 389 |
| 5 | 114 | 263 | 401 |
| 6 | 119 | 253 | 421 |
| 7 | 120 | 260 | 395 |
| 8 | 125 | 265 | 413 |
| 9 | 101 | 239 | 298 |
| 10 | 54 | 234 | 274 |
| 11 | 125 | 264 | 302 |
| 12 | 105 | 265 | 387 |
| 13 | 121 | 149 | 405 |
| 14 | 50 | 257 | 429 |
| 15 | 55 | 163 | 407 |
| Group No. 7 | | | |
| Chicken No. 1 | 110 | 253 | 430 |
| 2 | 122 | 233 | 345 |
| 3 | 106 | 238 | 386 |
| 4 | 116 | 270 | 466 |
| 5 | 120 | 230 | 342 |
| 6 | 133 | 252 | 392 |
| 7 | 124 | 250 | 426 |
| 8 | 123 | 215 | 428 |
| 9 | 124 | 268 | 469 |
| 10 | 133 | 240 | 431 |
| 11 | 113 | 255 | 302 |
| 12 | 46 | 138 | 470 |
| 13 | 130 | 248 | 362 |
| 14 | 120 | 228 | 371 |
| 15 | — | — | — |
| Group No. 8 | | | |
| Chicken No. 1 | 103 | 237 | 322 |
| 2 | 112 | 206 | 381 |
| 3 | 91 | 234 | 382 |
| 4 | 97 | 219 | 401 |
| 5 | 107 | 246 | 289 |
| 6 | 96 | 229 | 372 |
| 7 | 112 | 195 | 285 |
| 8 | 104 | 197 | 363 |
| 9 | 102 | 235 | 314 |
| 10 | 109 | 219 | 398 |
| 11 | 119 | 240 | 352 |
| 12 | 107 | 197 | 366 |
| 13 | 113 | 172 | 360 |
| 14 | 105 | 225 | 321 |
| 15 | — | — | — |
| Group No. 9 | | | |
| Chicken No. 1 | 143 | 272 | 443 |
| 2 | 124 | 273 | 466 |
| 3 | 107 | 277 | 423 |
| 4 | 119 | 279 | 433 |
| 5 | 123 | 259 | 434 |
| 6 | 116 | 285 | 453 |
| 7 | 131 | 263 | 422 |
| 8 | 127 | 261 | 440 |
| 9 | 144 | 260 | 384 |
| 10 | 118 | 263 | 388 |
| 11 | 125 | 271 | 385 |
| 12 | 137 | 248 | 454 |
| 13 | 114 | 235 | 422 |
| 14 | 125 | 198 | 436 |
| 15 | 98 | 234 | 334 |
| Group No. 10 | | | |
| Chicken No. 1 | 116 | 275 | 355 |
| 2 | 117 | 302 | 392 |
| 3 | 126 | 274 | 385 |
| 4 | 132 | 258 | 371 |
| 5 | 116 | 251 | 395 |
| 6 | 122 | 265 | 382 |
| 7 | 126 | 236 | 341 |
| 8 | 133 | 226 | 430 |
| 9 | 119 | 264 | 385 |
| 10 | 104 | 271 | 348 |
| 11 | 127 | 267 | 412 |
| 12 | 128 | 246 | 331 |
| 13 | 134 | 264 | 364 |
| 14 | 132 | 281 | 383 |
| 15 | 105 | 223 | 413 |
| Group No. 11 | | | |
| Chicken No. 1 | 107 | 284 | 400 |
| 2 | 125 | 227 | 355 |
| 3 | 117 | 273 | 440 |
| 4 | 121 | 244 | 416 |
| 5 | 115 | 242 | 337 |
| 6 | 133 | 274 | 372 |
| 7 | 137 | 243 | 380 |
| 8 | 104 | 227 | 426 |
| 9 | 113 | 250 | 424 |
| 10 | 125 | 252 | 357 |
| 11 | 131 | 254 | 430 |
| 12 | 128 | 226 | 481 |
| 13 | 114 | 224 | 340 |
| 14 | 112 | 226 | 394 |
| 15 | 119 | 249 | 349 |
| Group No. 12 | | | |
| Chicken No. 1 | 116 | 238 | 348 |
| 2 | 113 | 198 | 438 |
| 3 | 107 | 233 | 343 |
| 4 | 115 | 202 | 402 |
| 5 | 121 | 240 | 391 |
| 6 | 125 | 251 | 354 |
| 7 | 115 | 213 | 372 |
| 8 | 111 | 225 | 328 |
| 9 | 104 | 220 | 286 |
| 10 | 121 | 195 | 356 |
| 11 | 102 | 221 | 324 |
| 12 | 125 | 194 | 380 |
| 13 | 108 | 229 | 365 |
| 14 | 110 | 211 | 395 |
| 15 | 118 | 222 | 318 |
| Group No. 13 | | | |
| Chicken No. 1 | 121 | 226 | 394 |
| 2 | 116 | 233 | 431 |
| 3 | 118 | 236 | 438 |
| 4 | 122 | 225 | 416 |
| 5 | 125 | 230 | 445 |
| 6 | 118 | 232 | 443 |

TABLE 18-continued

WEIGHT OF CHICKENS

|  | wt. at 7 days, gm. | wt. at 14 days, gm. | wt. at 21 days, gm. |
|---|---|---|---|
| 7 | 137 | 222 | 435 |
| 8 | 112 | 213 | 392 |
| 9 | 113 | 241 | 435 |
| 10 | 127 | 227 | 427 |
| 11 | 116 | 212 | 413 |
| 12 | 113 | 218 | 390 |
| 13 | 127 | 228 | 404 |
| 14 | 123 | 248 | 422 |
| 15 | 108 | 216 | 415 |

Group No. 14

| Chicken No. | | | |
|---|---|---|---|
| 1 | 116 | 305 | 490 |
| 2 | 114 | 268 | 500 |
| 3 | 110 | 256 | 482 |
| 4 | 62 | 240 | 506 |
| 5 | 118 | 283 | 392 |
| 6 | 121 | 244 | 432 |
| 7 | 122 | 253 | 425 |
| 8 | 125 | 267 | 423 |
| 9 | 114 | 292 | 455 |
| 10 | 133 | 279 | 400 |
| 11 | 138 | 273 | 442 |
| 12 | 111 | 243 | 477 |
| 13 | 127 | 154 | 309 |
| 14 | 130 | — | — |
| 15 | — | — | — |

Group No. 15

| Chicken No. | | | |
|---|---|---|---|
| 1 | 32 | 281 | 453 |
| 2 | 128 | 280 | 439 |
| 3 | 116 | 277 | 328 |
| 4 | 109 | 215 | 410 |
| 5 | 132 | 273 | 450 |
| 6 | 134 | 280 | 348 |
| 7 | 49 | 244 | 386 |
| 8 | 136 | 262 | 447 |
| 9 | 138 | 247 | 417 |
| 10 | 108 | 211 | 444 |
| 11 | 116 | 214 | 400 |
| 12 | 128 | 252 | 337 |
| 13 | 117 | 146 | 291 |
| 14 | 107 | — | — |
| 15 | 111 | — | — |

Group No. 16

| Chicken No. | | | |
|---|---|---|---|
| 1 | 118 | 272 | 414 |
| 2 | 92 | 219 | 369 |
| 3 | 116 | 145 | 381 |
| 4 | 131 | 226 | 374 |
| 5 | 126 | 231 | 249 |
| 6 | 129 | 206 | 449 |
| 7 | 105 | 268 | 364 |
| 8 | 123 | 224 | 353 |
| 9 | 109 | 219 | 325 |
| 10 | 132 | 245 | 306 |
| 11 | 114 | 232 | 330 |
| 12 | 111 | 228 | 379 |
| 13 | 115 | 219 | 353 |
| 14 | 101 | 203 | 318 |
| 15 | 107 | 202 | 328 |

The feed consumed by the birds is given in the following table:

TABLE 19

Gms. Feed Consumed to 21 Days (No/Group) (Gm/Bird)

| Aflatoxin PPM | PPM Gentian Violet | | | |
|---|---|---|---|---|
| | 0 | 7 | 14 | 21 |
| 0 | 9,000 (15) (600) | 8,300 (15) (553) | 9,230 (15) (615) | 8,970 (15) (598) |
| 1 | 8,697 (15) (580) | 8,595 (15) (573) | 9,005 (15) (600) | 8,654 (13) (666) |
| 2 | 8,460 (15) (564) | 8,230 (14) (588) | 8,555 (15) (570) | 8,030 (13) (618) |
| 3 | 7,547 (14) (539) | 7,296 (14) (521) | 7,823 (15) (522) | 7,447 (15) (496) |

The average weight of each group of chicks over the test period is given in the following table:

TABLE 20

| Aflatoxin PPM | Age Days | Ave Weights-Grams PPM Gentian Violet | | | |
|---|---|---|---|---|---|
| | | 0 | 7 | 14 | 21 |
| 0 | 7 | 112.0 | 106.5 | 123.4 | 119.7 |
| | 14 | 241.3 | 228.9 | 258.5 | 242.3 |
| | 21 | 392.7 | 384.1 | 421.1 | 420 |
| 1 | 7 | 116.3 | 104.2 | 122.5 | 117.2 |
| | 14 | 255.6 | 236.3 | 260.2 | 237.2 |
| | 21 | 399.9 | 383.7 | 379.1 | 441 |
| 2 | 7 | 112.5 | 114.1 | 118.7 | 100.7 |
| | 14 | 230.7 | 238.3 | 246.2 | 228.3 |
| | 21 | 382.8 | 401.4 | 393.4 | 396.2 |
| 3 | 7 | 110.9 | 104.9 | 114.0 | 115.3 |
| | 14 | 206.3 | 217.9 | 219.5 | 222.6 |
| | 21 | 347.1 | 350.4 | 360.0 | 352.8 |

The sparing effect of gentian violet appears to be a linear function of the concentration of aflatoxin in the feed (administered or consumed). The groups receiving the gentian violet are significantly heavier than the groups not receiving gentian violet when they were fed B-1 aflatoxin.

EXAMPLE 5

Several rats were offered rat feed containing 1,000 PPM of gentian violet — the rats refused to eat the feed.

Several dogs were offered dog feed containing 1,000 PPM of gentian violet — the dogs refused to eat the feed.

This shows that animals will often refuse to eat feed containing high (toxic) levels of gentian violet.

What is claimed is:

1. A method for sparing poultry from the toxic effect of a mycotoxin in a complete poultry feed which comprises feeding said complete poultry feed to said poultry, said complete feed consisting of (i) gentian violet, and (ii) the remainder medically inert ingredients, said gentian violet sparing said poultry from the effect of said mycotoxin in said feed as a contaminant, the gentian violet being present in said feed in an amount between 0.00077 and 0.00385 by weight based on the weight of said feed.

2. A method as described in claim 1 which further comprises preparing a premix concentrate for addition to said feed which consists only of between 0.1 and 10 percent by weight of gentian violet and the remainder inert ingredients, and adding enough of said premix concentrate to the other ingredients of said feed to obtain the recited amount of gentian violet in said feed.

3. A method as described in claim 2 wherein said inert ingredients include diatomaceous silica, corn cob fractions and white mineral oil.

4. A method as described in claim 1 wherein said feed contains 0.00156 percent by weight of gentian violet, based on the weight of said complete poultry feed.

5. A method as described in claim 1 wherein said feed contains 0.00232 percent by weight of gentian violet, based on the weight of said complete poultry feed.

6. A method as described in claim 1 wherein said mycotoxin is aflatoxin.

7. A method as described in claim 1 wherein said feed is contaminated with as much as 10 PPM of said mycotoxin.

* * * * *